United States Patent [19]

Gavras et al.

[11] Patent Number: 5,070,187

[45] Date of Patent: Dec. 3, 1991

[54] PHARMACOLOGICALLY EFFECTIVE ANTAGONISTS OF ARGININE-VASOPRESSIN

[75] Inventors: Haralambos Gavras, Marblehead; Bernard Lammek, Newtonville, both of Mass.

[73] Assignee: Trustees of Boston University, Boston, Mass.

[21] Appl. No.: 431,421

[22] Filed: Nov. 3, 1989

[51] Int. Cl.$^5$ .................... C07K 7/16; C07K 7/06; A61K 37/34
[52] U.S. Cl. ........................ 530/315; 530/317; 530/328; 530/329; 530/330
[58] Field of Search ............ 530/315, 317, 328, 329, 530/330; 514/11, 15, 16, 17

[56] References Cited

U.S. PATENT DOCUMENTS

| | | | |
|---|---|---|---|
| 4,543,349 | 9/1985 | Callahan et al. | 514/11 |
| 4,851,409 | 7/1989 | Young et al. | 514/228.2 |
| 4,876,243 | 10/1989 | Marshall et al. | 514/11 |

FOREIGN PATENT DOCUMENTS 0061356  9/1982  European Pat. Off. .

OTHER PUBLICATIONS

Lowbridge et al., Journal of Medicinal Chemistry, 1978, vol. 21, No. 3, pp. 313-315.
Huffman et al., Journal of Medicinal Chemistry 1989, vol. 32, No. 4, pp. 880-883.
Lammek et al., J. Med. Chem. 1988, vol. 31, No. 3, pp. 603-606.
Lammek and Wang et al., Peptides, 1989, vol. 10, pp. 1109-1112.
J. Ridinger, Peptide Hormones, Univ. Park Press, Baltimore, J. A. Parsons (Edit), Jun. 1976, pp. 1-7.
Lammek et al., *Pol. J. Chem.*, 64:351 (1990).
Yim & Huffman, *Int. J. Pept. Prot. Res.* 21:568 (1983).
Nestor et al., *J. Med. Chem.* 18:284 (1975).
Vavrek et al., *J. Med. Chem.:* 15:123 (1972).

*Primary Examiner*—John Doll
*Assistant Examiner*—Avis Davenport
*Attorney, Agent, or Firm*—David Preshker

[57] ABSTRACT

A unique class of vasopressin analogue antagonists is provided which have the pharmacological property in-vivo to antagonize pressor ($V_1$) and/or antidiuretic ($V_2$) activities. The chemical modifications to the vasopressin 9 member chain sequence at the no. 1, 2, and 4 positions yield a class of potent analogue antagonists which may be employed therapeutically to treat hypertension, congestive heart failure, various edematous situations, and a variety of symptoms due to inappropriate vasopressin secretion.

3 Claims, No Drawings

PHARMACOLOGICALLY EFFECTIVE ANTAGONISTS OF ARGININE-VASOPRESSIN

RESEARCH SUPPORT

Investigative efforts for the present invention were supported by a research grant from the National Institute of Health (grant HL18-318).

FIELD OF THE INVENTION

The present invention is concerned generally with the design and synthesis of potent and effective vasopressin antagonists; and is particularly directed to the synthesis and methods of using vasopressin antagonists modified to eliminate both pressor ($V_1$) activity and antidiuretic ($V_2$) activities.

BACKGROUND OF THE INVENTION

Vasopressin is a naturally occurring peptide hormone released by the posterior pituitary gland in response to conditions of rising plasma tonicity or falling blood pressure. Vasopressin is a nonapeptide possessing at least two distinctly different kinds of pharmacological properties: the vasopressor ($V_1$) effect causing increases in blood pressure; and the antidiuretic ($V_2$) effect which brings about reabsorption of free water in the renal tubule. Any pathological lesion that reduces the secretion of vasopressin to levels that are less than approximately 7% of normal will produce clinically apparent diabetes insipidus. Trauma, surgery in the region of the pituitary and hypothalamus, malignancy, and infiltration lesions are well-recognized causes of this condition; there are also familial and idiopathic varieties of the disease. Regardless of specific cause, the pathophysiology remains the same: polyurea and the excretion of a dilute urine.

The present therapy of choice for treating pituitary diabetes insipidus is the administration of either a naturally occurring vasopressin or a vasopressin analogue which is synthetically produced. Naturally occurring vasopressin and synthetically prepared vasopressin analogues are also effective in some cases of esophagal variceal bleeding and of colonic diverticular bleeding. Current medical practice utilizes both naturally occurring vasopressins and a variety of different synthetically produced vasopressin analogues as selective therapeutic agents based upon research investigations conducted over the last forty years. In order to better understand the goals, purposes, advantages, and achievements of the present invention, it is useful to briefly summarize the present state of knowledge concerning the chemistry and the pharmacodynamics of vasopressin and its various synthetic analogues in living subjects, particularly humans.

Naturally occurring vasopressin was structurally analyzed and completely synthesized in the laboratory by du Vigneaud and co-workers by 1954 [*J. Am. Chem. Soc.* 75:4879-4880 (1953); *J. Am. Chem. Soc.* 76:4751-4752 (1954)]. In all mammals except those in the order suina, the naturally occurring structure is [8-arginine]-vasopressin (hereinafter "AVP") having the formula of:

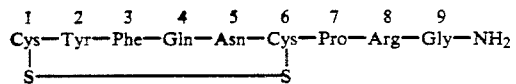

The naturally occurring peptide in the order suina was found to be [8-Lysine] vasopressin and has come to be termed "Lypressin." All naturally occurring vasopressins are nonapeptides with two cysteine residues forming a bridge between positions 1 and 6 respectively. Integrity of the disulfide bond is usually thought to be essential for retention of biological activity [*The Pharmacological Basis Of Therapeutics*, 7th edition (Goodman et al., editors), MacMillan Publishing Company, New York, 1985, pages 908-919]. However, it was recently reported that an intact S-S ring is not necessary for binding of antagonistic AVP analogues [Manning et al., *Nature* 329:839-840 (1987)].

The natural vasopressins such as AVP are subject to rapid enzymatic degradation in-vivo. Four sites of cleavage have been identified, the most important of which appear to be at positions 7-8 and 8-9 in the peptide; the disulfide bond and positions 1-2 are also sites of attack by a variety of different enzymes in the kidney, brain, liver, and uterus. The half-life of circulating vasopressin is approximately 20 minutes, with renal and hepatic catabolism occurring via reduction of the disulfide bond and peptide cleavage. A small amount of vasopressin is normally excreted, as in the urine, but urinary clearance is less than 5% of that occurring elsewhere in the body.

Naturally occurring vasopressins such as AVP interact primarily with two distinct receptor types in the organs and tissues of the body designated as $V_1$ and $V_2$ respectively [Michel et al., *Biochem. Soc. Trans.* 7:861-865 (1979)]. $V_1$ receptors have been identified on vascular smooth muscle and in liver cells [Schiffrin and Genest, *Endocrinology* 113:409-411 (1983); Cantau et al., *J. Recept. Res.* 1:137-168 (1980)]. The stimulation of $V_1$ receptors caues constriction of blood vessels and an increase of blood pressure. Alternatively, $V_2$ receptors are located in the renal tubule [Guillon et al., *Eur. J. Pharmacol.* 85:291-304 (1982)]. The stimulation of $V_2$ receptors in the kidney brings about reabsorption of free water in the renal tubule—the so called antidiuretic effect mediated by the formation of cyclic AMP. Much research effort has been devoted to investigating the mechanisms of receptor activation [Jard, S., *Progress In Brain Research* 60:383-394 (1983) and the references cited therein].

Another very active area of investigation has been the design and synthesis of specific vasopressin analogues which function as selective agonists or antagonists for each receptor type. This latter area of investigation has become the primary focus of investigators for designing and synthesizing pharmacologically active preparations [Manning and Sawyer, "Development Of Selective Agonists And Antagonists Of Vasopressin And Oxytocin," in Vasopressin (Robert W. Schrier, editor), Raven Press, New York, 1985, pages 131-144 and the references cited therein].

It is useful to recognize and note the basic distinction between synthetically prepared vasopressin agonists and to distinguish them from synthetically prepared vasopressin antagonists. By definition, vasopressin agonists are able to selectively act upon and activate a given receptor type, either $V_1$ or $V_2$, in order to mimic only the antidiuretic effect or the pressor effect alone. Perhaps the best known example of a $V_2$ agonist is the widely used analogue, [1-deamino,8-D-arginine] vasopressin, termed "dDAVP" in research investigations and "desmopressin" as the trade name drug [Zaoral et al., *Coll. Czech. Chem. Commun.* 32:1250-1257 (1967)].

Contradistinctively, a vasopressin antagonist by definition is a vasopressin analogue which will selectively bind to but *not activate* a given receptor type (either $V_1$ or $V_2$); and which will therefore block agonistic responses at the selective receptor site [Lowbridge et al., *J. Med. Chem.* 21:313-315 (1978); Manning et al., *J. Med. Chem.* 20:1228-1230 (1977)]. Although structural parallels between agonists and antagonists of vasopressin can be drawn, it is critical to always differentiate and distinguish between the two in terms of functional and pharmacological effects.

Considerable interest and investigations have been directed to developing vasopressin analogues which are selective for either $V_1$ or $V_2$ receptors; and which are also either agonists or antagonists of only a single type of receptor ($V_1$ or $V_2$ but not both) [see Manning, M. and W. H. Sawyer, "Development Of Selective Agonists And Antagonists Of Vasopressin And Oxytocin," in *Vasopressin* (R. W. Schrier, editor), Raven Press, New York, 1985, pp 131-144; U.S. Pat. Nos. 4,543,349 and 4,658,015; and Lammek et al., *J. Med. Chem.* 31:603-606 (1988)]. Based on these developments, the critical structural requirements for substantial antidiuretic antagonism of cyclic analogues of AVP appear to involve a combination of the following modifications: a 1-mercaptocyclohexaneacetic acid residue at position 1; either D-Tyr(Et), D-Phe, D-Leu, or D-Ile at position 2; and an amino acid residue such as Val, Ala, Abu ($\alpha$-amino-butyric acid), etc. at position 4. One of the presently known potent antagonists of the antidiuretic and pressor responses to AVP [Manning and Sawyer, supra] has the following structure:

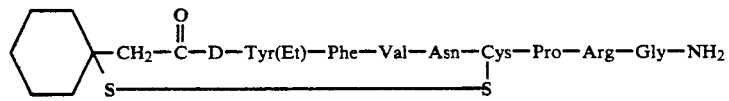

This Manning formulation, however, represents the current limits of our knowledge and developments in this art. This general structure, together with minor substitutions at position 1 and appropriate modifications of positions 2 and 4 respectively result in anti-antidiuretic analogues of AVP. Accordingly, there remains a clear and present need for highly potent compositions having anti-vasopressor ($V_1$) and anti-antidiuretic ($V_2$) antagonistic properties which are demonstratably pharmacologically active after administration in-vivo. The generation of such novel potent compositions would be recognized generally as a major advance and improvement over the currently available choices by practitioners ordinarily skilled in this art.

SUMMARY OF THE INVENTION

A new class of vasopressin analogues is provided which have pharmacological potency in-vivo to antagonise pressor ($V_1$) and/or antidiuretic ($V_2$) activities, said class of vasopressin antagonists comprising the formula:

wherein X is selected from the group consisting of an oxygen atom and a sulfur atom;

Y is an amino acid residue selected from the group consisting of D-valine, D-$\alpha$-amino butyric acid, D-leucine, D-isoleucine, D-tyrosine, o-alkyl-D-tyrosine wherein said alkyl group comprises from 1-6 carbon atoms, and R-D-phenylalanine wherein said R is a moiety selected from the group consisting of hydrogen, a halogen, and an alkyl group comprising 1-6 carbon atoms; and Z is an amino acid residue selected from the group consisting of $\alpha$-amino butyric acid, valine, alanine, threonine, leucine, and isoleucine.

DETAILED DESCRIPTION OF THE PREFERRED EMBODIMENTS

The present invention provides a new class of vasopressin analogue antagonists—all of which have antipressor ($V_1$) properties and most of which also possess anti-antidiuretic ($V_2$) capability. The chemical class of analogues provides major modifications to the acid entity located at position 1 of the 9 member chain sequence in combination with previously known substitutions of the amino acid residues employed at positions 2 and 4 respectively within the 9 member chain comprising the vasopressin analogue.

With these chemical modifications and substitutions, a novel class of antagonistic vasopressin analogues are presented which provide major advances and unique benefits to the user. These advantages and benefits include the following:

1. Different steric structure for the substituent at position 1: Position 1 of $V_2$ antagonists appears to be extremely important for the peptide-receptor interaction. This has been demonstrated by our studies and those of other scientists [Huffman et al., *J. Med. Chem.* 32:880-884 (1989)]. Modifications in the steric structure of the substituent at position 1 sometimes lead to peptides which will interact differently with $V_2$ receptor and thus they may sometimes turn out to have $V_2$ antagonistic activity in humans. Previous efforts to produce effective antagonists of the antidiuretic response to AVP in humans have yielded disappointing results [Huffman, et al., *J. Med. Chem.* 32:880-884 (1989)]; as a noteworthy example, the evaluation in human volunteers of a potent $V_2$ antagonist namely [1-(1-mercaptocyclohexaneacetic acid)-2-(O-ethyl-D-tyrosine), 4-valine, -desglycine)-8-arginine vasopressin] revealed that this analogue behaved as a $V_2$ agonist rather than $V_2$ antagonist.

2. The modification of position 1 results in highly effective antagonists in-vitro: 4-thio-4-tetrahydrothiopyrane-acetic acid modification of position 1 is advantageous in comparison to the 4-mercaptocyclohexanea-

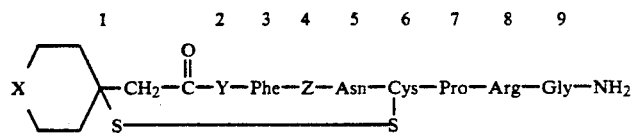

cetic acid substitution which is considered as one of the best presently known. This novel compound elicits a greater response especially at higher doses. Also, the 4-thio-4-tetrahydropyraneacetic acid substitution confers enhanced overall efficacy in terms of magnitude of effect.

3. The unique analogues have been found to retain their effectiveness in vivo using experimental animals: The present antagonistic analogues would be of value in the treatment of pathologic conditions associated with inappropriate or compensatory oversecretion of vasopressin (or both). Such conditions include hypertension, congestive heart failure (ranging from class II of the New York Heart Association to florid pulmonary edema), periodic idiopathic edema, nephrotic syndrome, ascites due to cirrhosis or other causes, cerebral edema of various causes, as well as dilutional hyponatremia and metabolic alterations collectively known as the syndrome of inappropriate ADH secretion.

One general definition of this unique class of analogue vasopressin antagonists is given by Formula I below:

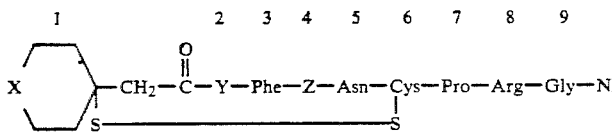

Wherein

X is either an oxygen atom or a sulfur atom;

Y is an amino acid residue and is one chosen from among the D-valine, D-α-aminobutyric acid, D-leucine, D-isoleucine, D-tyrosine, o-alkyl-D-tyrosine wherein the alkyl moiety comprises 1–6 carbon atoms, and R-D-phenylalanine wherein R is a moiety selected from the group consisting of hydrogen, a halogen (fluorine, bromine, chlorine, iodine) and an alkyl group comprising 1–6 carbon atoms; and Z is an amino acid residue chosen from among the α-amino butyric acid, valine, alanine, threonine, leucine, or isoleucine residues.

It will be recognized that a variety of diverse subclasses are encompassed by Formula I—the range of differences being provided by the choices of embodiments for the moieties located at positions 1, 2, and 4 respectively within the nine member chain sequence. Clearly, however, the selection of choices for the moiety located at position 1 in the sequence is in each instance limited to a thioacid residue, the formula and structure of which includes structures 1A and 1B respectively as given below:

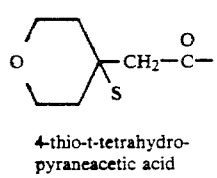

4-thio-t-tetrahydro-
pyraneacetic acid

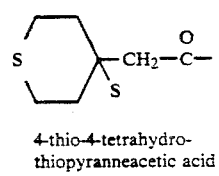

4-thio-4-tetrahydro-
thiopyranneacetic acid

In addition, the choices available for selection as embodiments at positions 2 and 4 respectively within the member chain sequence are varied. The most desirable entities located at position 2 are o-ethyl-D-tyrosine, D-phenylalanine, and D-isoleucine. Clearly, many different alkyl derivatives of D-tyrosine are also available in either linear or branched arrangements. Alternatively, D-tyrosine (non-alkyl forms), R-D-phenylalanine (R=alkyl or halogen), and D-leucine may also be usefully employed at position 2.

A similar range of choices exists for the amino acid residue located at position 4. Most preferred are α-amino butyric acid, D-valine, or D-isoleucine. Other possibilities include D-alanine, D-threonine, or D-leucine. All of these will provide potent vasopressin antagonists in varying degrees of efficacy.

It will be noted and appreciated that other broad definitions of effective analogue vasopressin antagonists are also provided by the present invention.

A second general definition of this unique class is provided by Formula II below:

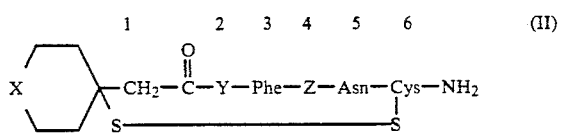

wherein X, Y, and Z are as described previously within Formula I. It is apparent, however, that Formula II provides a six member chain vasopressin analogue whose pharmacological activity is expected to be somewhat less than the 9 member residue sequence counterpart described previously.

A third general definition of the present invention recognizes and concerns itself with residue variability in positions 7–9 respectively following the cysteine residue at position 6 in the analogue sequence. It is expected that the nos. 7–9, "tail section," of the analogue formulation may be greatly varied in composition and in choice of amino acid residues employed; and other non-amino acid substituents may even be used to lengthen and extend the membership of the sequential chain. This definition is provided by Formula III below:

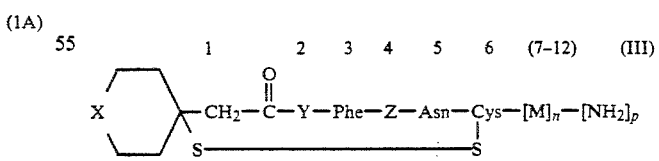

wherein

M is a substituent comprising at least one amino acid residue and n is a number from 0–6, and P is either 0 or 1; and X, Y, and Z are as previously described herein.

Representative of M's variety and exemplifying the number of substituents and residues able to be employed alternatively at positions 7–12 are those listed within Table 1 below. It will be recognized and appreciated also that Formula III permits the user to construct at will 7 member, 8 member, or 9 member chains; and using non-amino acid substituents to form 10 member, 11 member, or even 12 member chain sequences as the desires or circumstances demand. All of these 7-12 member residue chains are within the scope of the present invention.

TABLE I

| AT POSITION NUMBER | CHOICE OF RESIDUE |
|---|---|
| 7 | Proline; dehydroproline; sarcosine; and an absence of proline completely. |
| 8 | Lysine; D-lysine; D-arginine; and an absence of arginine completely. |
| 9 and end sequence | An absence of glycine; an absence of glycine-$NH_2$; $NH-(CH_2)_2-NH_2$; Gly—NH—$(CH_2)_2$—$NH_2$; $NH-(CH_2)_2-OH$; Gly—NH—$(CH_2)_2$—OH; Gly—NH—$CH_3$; Gly—Gly—$(NH_2)_2$; —Ala—$(NHCH_2)$; —Ala—$NH_2$; Sar—$(NHCH_3)$; Ala; Tyr (also diiodotyrosine or iodotyrosine) Orn; Ser; Val; Phe; Ile; Thr; and Pro |

The synthesis, purification, and confirmation of formulation for all these vasopressin analogues are conventionally known in the art. Moreover, although the antagonistic activity and in-vivo effectiveness will range greatly with the individual choice of formulation. It is expected that each member of this defined class of vasopressin analogues will exhibit some meaningful degree of $V_1$ antagonistic pharmacological activity.

In-vivo administration with any embodiment of the class of vasopressin antagonists defined by Formulas I—III is a general methodology to therapeutically antagonize pressor ($V_1$) or pressor ($V_1$) and antidiuretic ($V_2$) effects in living subjects, particularly humans. The preferred route of administration is intravenous infusion or parenteral introduction of the antagonist by intravenous infusion, syringe injection, or other conventionally known means. An alternate route of administration is by intranasal spray where it was shown to have adequate and significant absorbability.

In general, the concentration of the chosen vasopressin antagonist encompassed by Formula I which may be effectively employed for therapeutic treatment of living subjects is expected to be 50-500 ug/kg body weight.

To demonstrate the efficacy and value of the novel class of vasopressin antagonists comprising the present invention for therapeutic treatment of pressor ($V_1$) and antidiuretic ($V_2$) effects, a variety of in-vivo experiments will be described. It will be clearly understood, however, that these experimental examples are merely representative of the diverse formulations, efficacy, and advantages provided by the present invention; and serve merely to illustrate the variety of operative conditions and clinical applications with which the vasopressin antagonists can be usefully employed. Under no circumstances, however, are the specific test conditions or empirically obtained results to be deemed as restricting or limiting the present invention in any manner.

EXPERIMENTAL SERIES

Among the single modifications that have been shown to be essential for antidiuretic antagonism of cyclic analogues of AVP is the 1-mercaptocyclohexaneacetic acid substitution at position 1 [Manning et al., In *Vasopressin*, edited by R. W. Schrier, New York, Raven Press, pp 131-144 (1985)]. However, evaluation in human volunteers of a potent vasopressin $V_2$ receptor antagonist that has this residue at position 1, namely [1-(1-mercaptocyclohexaneacetic acid),2-(0-ethyl-D-tyrosine),4-valine,9-desglycine]-8-arginine vasopressin, revealed that this peptide behaved as a $V_2$ agonist rather than a $V_2$ antagonist [Huffman et al., *J. Med. Chem.* 32:880-884 (1989)].

Recently, the empirical evidence provided by in-house studies [Lammek et al., in press] showed that even relatively minor modifications of residues occupying position 1 are extremely important for anti-antidiuretic activity of the peptide analogues. The dramatic changes in $V_2$ antagonistic activity of the peptide analogues differing only by the presence of $CH_3$ (highly active) or $C(CH_3)_3$ (inactive) groups in position 4 of the cyclohexane ring of the substituent at position 1 proves it unequivocally.

A recent publication from Huffman et al. [*J. Med. Chem.* 32:880-884 (1984)] indicates that such subtle differences in the structure of the 1-mercaptocyclohexaneacetic acid occupying position 1 can result in a major decrease of undesired agonistic activity. They discovered that the presence of a cis-4-methyl group on the 1-mercaptocyclohexaneacetic acid residue at position 1 of a $V_2$ vasopressin antagonist results in reduced agonist activity compared to the unsubstituted peptide. All these findings once more point to the importance of the structure of the residue at position 1 for the $V_2$ activity of cyclic AVP analogues. It is possible that if further modifications of position 1 can eliminate the agonistic activity obtained in humans with cyclic analogues, such peptides might be suitable for acute and/or chronic use in the treatment of disease states associated with abnormalities in water metabolism (e.g., dilutional hyponatremia, etc.) resulting from inappropriate or compensatory over secretion of AVP.

With this in mind, two new analogues were synthesized which have located in position 1 new thioacids recently developed; and D-Tyr(Et) and Val at positions 2 and 4 respectively. These analogues are as follows: [1-(4-thio-4-tetrahydropyraneacetic acid), 2-0-ethyl-D-tyrosine,4-valine]-8-arginine vasopressin and [1-(4-thio-4-tetrahydrothiopyraneacetic acid),2-0-ethyl-D-tyrosine-4-valine]-8-arginine -vasopressin. These peptides have the general structure of Formula I as follows:

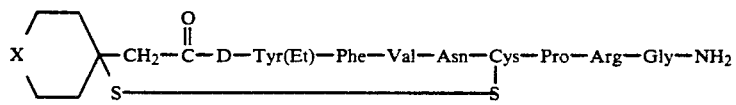

Wherein X = O (Formula 1A); or
Wherein X = S (Formula 1B).

The presence of the heteroatom within the cyclic carbon ring structure of position 1 substantially influences the interaction of the peptide as a whole with the $V_2$ receptor; and, therefore, increases the efficacy and selectivity of the analogues. Pharmacological studies showed that peptide analogues 1A and 1B are among the most potent and effective $V_2$ antagonists of AVP. Changes of position 1 may be also combined with many different substitutions at positions 2 and 4; and such antagonists can have either other deletions or substitutions in the remainder of the peptide chain to form a wide variety of derivatives.

PEPTIDE SYNTHESIS

The protected peptide precursors required for the synthesis of peptide analogues 1A and 1B were prepared by the solid-phase method of peptide synthesis entirely on the resin [Manning, M., *J. Am. Chem.* 90:1348-1349 (1968); Merrifield, R., *J. Am. Chem. Soc.* 85:2149-2154 (1963)]. Chloromethylated resin (Bio-Rad, Bio Beads S×1) was esterified with BOC-Gly to a load of 0.42 mmol/g. BOC-Gly resin was converted to protected acyl octapeptidylresins in eight cycles of solid phase synthesis. Coupling reactions were mediated by the DCC/HOBt method. The completeness of each coupling reaction was monitored by the Kaiser test 4-[(p-metoxy-phenylmethyl)thio]-4-tetrahydropyraneacetic acid and 4-[(p-metoxyphenylmethyl)thio]-4-tetrahydrothiopyraneacetic acid were each used in the final coupling steps. After completion of the synthesis the protected acyl octapeptidyl resins were ammonolyzed in methanol as conventionally known. Following evaporation of the solvent, the products were extracted into hot DMF, precipitated with boiling water, and left overnight at room temperature. The peptides were collected by filtration, washed with water, and dried in vacuo over $P_2O_5$. The products were further purified by dissolving in DMF and reprecipitating with MeOH/ethyl ether (1:3).

Each protected precursor was then deblocked with sodium in liquid ammonia [Manning et al., *Biochemistry* 9:3925 (1970)] and the resulting sulfhydryl compounds were subjected to oxidative cyclization with the potassium ferricyanide. The crude peptides were first desalted on Sephadex G-15 and then purified on Sephadex LH-20. The data from amino acid analysis of both analogues revealed the expected ratios of amino acids. The purity of both peptides was checked on TLC using three different systems.

BIOASSAY METHODS

Intact male Wistar rats (Charles River Breeding Laboratories, Wilmington, Mass., U.S.A.) weighing 300-400 g were used and maintained on a regular Purina rat chow diet as well as tap water in a room at constant temperature (23 ±1° C.) with 12 h dark/12 h light cycles.

The anti-antidiuretic potencies of analogues were evaluated by their ability to inhibit the antidiuretic effect of endogenous AVP. The rats were individually housed in metabolic cages on the day preceding the experiment with free access to food and water. On the day of the experiment, the animals were weighed and received an intraperitoneal injection of sterile 5% dextrose (1 ml/kg). Urine was collected continuously over two 1.5 h periods (3 hours) as a baseline. Upon completion of this period, one dose of analogue was injected intraperitoneally. Urine was collected continuously at 1.5 h intervals until it recovered to the baseline. This procedure was repeated every other day with a different dose of the same analogue in the same rat. Different doses of every analogue were tested. The peak response to each dose which usually occurred during the second 1.5 h period was used for evaluation. The $V_2$ antagonistic activity of these analogues is expressed as the effective dose ($ED_6$, in nmol/kg) which increases urine volume from a baseline average of 1.2±0.05 ml/1.5 h (n-169) to 6 ml/1.5 h.

Concurrently, the antivasopressor potency of these analogues was assessed by their ability to inhibit the pressor response to exogenous vasopressin. The right iliac artery and jugular vein were catheterized with polyethylene tubing (PE 50) in rats under light ether anesthesia on the day preceding the experiment. On the day of the experiment, the rats were maintained conscious and unrestrained in plastic cages. Blood pressure and heart rate were monitored through a Gould-Statham P23 ID pressure transducer (Gould, Cleveland, Ohio, U.S.A.) connected to the iliac catheter and recorded on a Gould 2200S paper chart recorder. An one-hour stabilization period was observed before the actual initiation of the experiment. (Arg 8 8)-Vasopressin acetate salt (Sigma), dissolved in 5% dextrose to a concentration of 50 mU/ml, was injected into the jugular vein. Two doses of AVP, 2.5 mU and 5.0 mU, were given randomly every 15 to 20 minutes. Each dose was repeated for two to three times until the pressor response was stable. Two average values of the pressor responses to these two doses of AVP were taken respectively as the control values. One dose of analogue was injected via the iliac catheter with a volume less than 0.5 ml, flushed with 0.1 ml 5% dextrose. Then 5 mU of AVP was injected 15, 30, 60, 120, 180, 240, min. respectively after the administration of the analogue until the pressor response to 5 mU AVP returned to the control level. On the second day, the same rat was tested in the same way with another dose of the same analogue aiming for a dose of the analogue that would reduce the pressor responses to 5 mU AVP to a point between the control response to 5.0 mU AVP and to 2.5 mU AVP. Subsequently, another dose of the analogue was sought, that would further reduce the pressor response to 5 mU AVP at a point below the control response to 2.5 mU AVP but would not eliminate it completely. The values obtained at 15 min. after the administration of the AVP antagonist were used for evaluation. The anti-$V_1$ receptor potency of each analogue is expressed as the effective dose (ED) and the $pA_2$, according to the principle of Schild [*Brit. J. Pharmacol.* 2:189-206 (1947)]. The ED is defined as the dose (in nmol/kg) that reduces the response to two units of agonist (5.0 mU of AVP) to equal the response to one unit of agonist (2.5 mU of AVP). The $pA_2$ value represents the negative logarithm of the molar concentration of the effective dose, i.e., the negative logarithm of the ED value divided by the estimated volume of distribution (67 ml/kg).

RESULTS

The antivasopressor and anti-antidiuretic potencies of the new analogues I and II together with these properties of [1-(-mercaptocyclohexaneacetic acid),2-(0-ethyl-D-tyrosine),4-valine]-8-arginine vasopressin [d($CH_2$)$_5$D-Tyr(Et)VAVP](8) which was used for comparison are presented in Table 2. Both analogues are antidiuretic antagonists. Comparison of $ED_6$ of these peptides indicates that both substitutions result in decreased potency (increased values of $ED_6$) but increased overall efficiency because of enhanced effectiveness at higher concentrations compared to the reference peptide. The increases in urinary flow rate elicited by the two new analogues and the reference peptide are shown in Table 3. The maximal response to the reference peptide was achieved with 50 ug/Kg dose and higher concentration produced no greater response. The urinary flow rate caused by SCADTyr(Et)VAVP (II) at the same concentration was similar; however, the latter peptide produced further increase in flow rate at higher concentration and the maximum effect was accomplished when the concentration reached 100 ug/Kg. The urinary flow rate caused by OCADTyr(Et)VAVP (I) in concentrations up to 100 ug/kg was lower compared to reference peptide, however, the maximum effect was accomplished with concentration 300 ug/kg and was greater than that of the reference peptide. The maximum effect of all peptides appeared at 3 hours. The recovery time for both new analogues was shorter compared to the reference peptide and depended on the concentration used.

Analogue II exhibits antivasopressor potency similar to that of the reference peptide while the antivasopressor potency of analogue I is significantly higher.

TABLE II
PHARMACOLOGICAL DATA OF AVP ANALOGUES

| ANA-LOGUE | VASOPRESSOR ($V_1$) | | | | ANTIDIURETIC ($V_2$) |
|---|---|---|---|---|---|
| | N | ED# | $pA_2$# | N | $ED_6$+ |
| I | 5 | 2.45 ± 0.57 | 7.57 ± 0.22 | 5 | 20.19 ± 5.11 |
| II | 5 | 5.17 ± 1.17 | 7.21 ± 0.18 | 6 | 14.23 ± 2.35 |
| Reference Peptide* | 5 | 3.88 ± 0.51 | 7.24 ± 0.055 | 5 | 12.65 |

N = number of rats tested with each compound.
The "effective dose" (ED) is defined as the dose (in nmol/Kg) that reduces the response to two units of agonist to the level obtained previously by one unit of agonist. The $pA_2$ values represent the negative logarithms of the ED values divided by the estimated value of distribution (67 ml/Kg) (9).
+The effective dose ($ED_6$) is the dose (in nmol/Kg) of analogue which increases volume from baseline to 6 ml/1.5 h (2).
*This compound was previously synthesized by Manning et al., supra.

compared to the conventionally known vasopressin antagonists.

Based on the data presented here for both analogues, it is clear that the 4-thio-4-tetrahydrothiopyraneacetic acid modification of position 1 of AVP antagonists (analogue II) is advantageous in comparison to the 1-mercaptocyclohexaneacetic acid substitution, which is considered as one of the most effective ones described so far. Although the $ED_6$ value of peptide II is slightly lower than that of the reference peptide, when the overall efficacy of the two compounds is compared the peptide II appears to be superior.

The peptide I, which differs from analogue II only by the presence of oxygen instead of sulfur in the cyclohexane ring of the substituent occupying position 1, clearly shows much weaker antagonistic potency; however, its efficacy is also greater than that of the reference peptide.

In summary, besides providing new information on structural requirements for residues occupying position 1 of AVP analogues for $V_2$ antagonism, these studies yielded novel effective $V_1/V_2$ antagonists which also have potential value as pharmacological probes of the actions of endogenous AVP.

The present invention is not to be restricted in form nor limited in scope except by the claims appended hereto.

We claim is:

1. A potent vasopressin analogue antagonist comprising the formula:

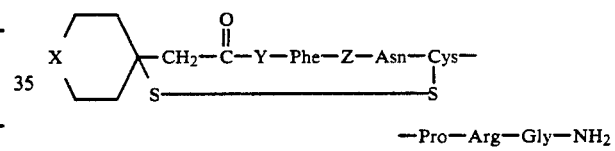

—Pro—Arg—Gly—$NH_2$ wherein
X is selected from the group consisting of an oxygen atom and a sulfur atom;
Y is an amino acid residue selected from the group consisting of D-valine, D-α-amino butyric acid,

TABLE III
AQUARETIC EFFECTS OF THE MANNING REFERENCE PEPTIDE (R) AND NEW ANALOGUES OF AVP [OCADTyr(Et)VAVP (I) AND SCADTyr(Et)VAVP (II)]

| | DOSE (ug/kg) | N | −1.5h | 1.5h | 3h | 4.5h | 6h | 7.5h |
|---|---|---|---|---|---|---|---|---|
| R | 10 | 5 | *1.14 ± 0.10 | 4.42 ± 1.51 | 4.6 ± 0.94 | 1.12 ± 0.14 | 0.85 ± 0.1 | |
| | 50 | 5 | 1.25 ± 0.19 | 6.40 ± 0.79 | 12.9 ± 0.92 | 7.74 ± 1.24 | 1.62 ± 0.36 | 0.93 ± 0.07 |
| | 100 | 5 | 0.93 ± 0.13 | 6.48 ± 1.12 | 12.66 ± 1.53 | 11.98 ± 2.91 | 4.9 ± 1.92 | 1.9 ± 0.43 |
| | 300 | 5 | 1.03 ± 0.24 | 4.40 ± 0.42 | 9.16 ± 1.74 | 12.4 ± 2.88 | 6.32 ± 2.29 | 2.95 ± 1.02 |
| I | 10 | 5 | 0.98 ± 0.21 | 4.14 ± 0.68 | 1.78 ± 0.16 | 1.03 ± 0.27 | | |
| | 50 | 5 | 1.24 ± 0.13 | 7.88 ± 0.91 | 9.0 ± 1.91 | 2.1 ± 0.50 | | |
| | 100 | 5 | 1.25 ± 0.18 | 7.08 ± 1.65 | 8.8 ± 1.63 | 5.4 ± 1.0 | | |
| | 300 | 5 | 1.19 ± 0.20 | 8.46 ± 1.39 | 15.62 ± 0.54 | 14.74 ± 1.7 | 4.24 ± 0.89 | 1.5 ± 0.5 |
| II | 10 | 5 | 1.21 ± 0.20 | 4.28 ± 0.49 | 4.12 ± 2.33 | | | |
| | 50 | 5 | 0.96 ± 0.08 | 7.4 ± 2.1 | 11.78 ± 1.13 | 4.38 ± 0.68 | 1.6 ± 0.3 | |
| | 100 | 5 | 1.0 ± 0.22 | 8.96 ± 1.04 | 18.02 ± 1.88 | 8.8 ± 1.31 | 2.2 ± 0.9 | |
| | 300 | 5 | 0.92 ± 0.21 | 7.28 ± 0.84 | 16.76 ± 1.05 | 2.8 ± 0.3 | 0.92 ± 0.08 | |

*The values in the table are volumes of urine in ml/1.5h (mean ± SEM) collected at intervals before and after injection of the peptide.
N = number of rats tested with each dose.

CONCLUSIONS

Analogues I and II were found to be potent and highly effective $V_1/V_2$ antagonists of AVP. The modification of position 1 combined with appropriate substitutions of position 2 and 4 gives superior $V_2$ antagonism D-leucine, D-isoleucine, D-tyrosine, and O-alkyl-D-tyrosine wherein said alkyl moiety comprises 1–6 carbon atoms, and R-D-phenylalanine wherein R is a moiety selected from the group consisting of a hydrogen atom, a halogen substituent, and an alkyl group comprising 1–6 carbon atoms; and Z is an amino acid residue selected from the group consisting of α-amino butyric acid, threonine, valine, alanine, leucine, and isoleucine.

2. A potent vasopressin analogue antagonist comprising the formula:

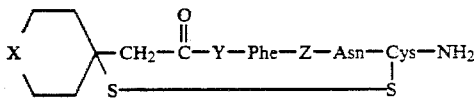

wherein
X is selected from the group consisting of an oxygen atom and a sulfur atom;
Y is an amino acid residue selected from the group consisting of D-valine, D-α-amino butyric acid, D-leucine, D-isoleucine, D-tyrosine, and O-alkyl-D-tyrosine wherein said alkyl moiety comprises 1–6 carbon atoms, and R-D-phenylalanine wherein R is a moiety selected from the group consisting of a hydrogen atom, a halogen substituent, and an alkyl group comprising 1–6 carbon atoms; and
Z is an amino acid residue selected from the group consisting of α-amino butyric acid, threonine, valine, alanine, leucine, and isoleucine.

3. A potent vasopressin analogue antagonist comprising the formula

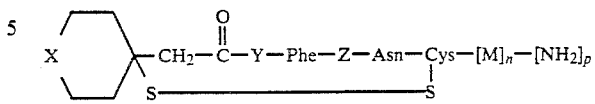

wherein
M comprises from 1–3 amino acid residues, at least one of said amino acid residues being selected from the group consisting of proline, dehydroproline, sarcosine, lysine and arginine, n is a number from 0–6, and p is either 0 or 1;
Y is an amino acid resdue selected from the group consisting of D-valine, D-α-amino butyric acid, D-leucine, D-isoleucine, D-tyrosine, o-alkyl-D-tyrosine where said alkyl moiety comprises 1–6 carbons, and R-D-phenylalanine wherein R is a moiety selected from the group consisting of a hydrogen atom, a halogen substituent, and an alkyl group comprising 1–6 carbon atoms; and
Z is an amino acid residue selected from the group consisting of α-amino butyric acid, threonine, valine, alanine, leucine, and isoleucine.

* * * * *